United States Patent [19]

Schreyer et al.

[11] 4,239,696

[45] Dec. 16, 1980

[54] PROCESS FOR THE PRODUCTION OF ALKYL SULFONIC ACIDS

[76] Inventors: Gerd Schreyer, Wildaustrasse 22; Friedhelm Geiger, Theodor-Heuss-Strasse 11; Jörg Hensel, Grünaustrasse 3, all of 6450 Hanau 9, Fed. Rep. of Germany

[21] Appl. No.: 655,017

[22] Filed: Feb. 4, 1976

Related U.S. Application Data

[63] Continuation-in-part of Ser. No. 654,063, Feb. 2, 1976, abandoned.

[30] Foreign Application Priority Data

Feb. 1, 1975 [DE] Fed. Rep. of Germany ....... 2504235

[51] Int. Cl.$^3$ ............................................. C07C 143/02
[52] U.S. Cl. ................................................. 260/513 R
[58] Field of Search ................................... 260/513 R

[56] References Cited

U.S. PATENT DOCUMENTS

| | | | |
|---|---|---|---|
| 2,667,507 | 1/1954 | Jones et al. | 260/513 R |
| 3,509,206 | 4/1970 | Nielsen | 260/502 R |

*Primary Examiner*—Nicky Chan
*Attorney, Agent, or Firm*—Cushman, Darby & Cushman

[57] ABSTRACT

Alkylsulfonic acids are prepared by oxidation of an alkyl mercaptan or dialkyl disulfide with hydrogen peroxide in an alkylsulfonic acid in the absence of percarboxylic acids and preferably employing 1 to 35 mole % of alkylsulfonic acid based on the alkyl mercaptan or dialkyl disulfide employed.

13 Claims, No Drawings

PROCESS FOR THE PRODUCTION OF ALKYL SULFONIC ACIDS

This application is a continuation-in-part of application Ser. No. 654,063, filed Feb. 2, 1976, now abandoned.

The present invention is directed to a process for the production of alkylsulfonic acids by the oxidation of alkyl mercaptans or dialkyl disulfides with hydrogen peroxide in the presence of alkylsulfonic acids.

Alkylsulfonic acids (also called alkanesulfonic acids) are of interest as strong, nonoxidizing acids, both as solvents and also as catalysts in alkylation, esterification and polymerization reactions.

Various processes are known for producing alkylsulfonic acids. Thus Koenig U.S. Pat. No. 2,892,852 describes the oxidation of organic thioethers and thioacetic acid esters with peracetic acid in acetic acid.

An oxidation of thiolacetates with performic acid also is known, see H. Nawa et al, J. Amer. Chem. Soc. 82, 896 (1960).

Still more expensive than the described processes are processes using potassium permanganate, nitric acid or ozone as the oxidizing agent, see Asinger, *J. Praktische Chemie* (4), Vol. 2, pages 241–242 (1955). The processes therefore are only slightly used for industrial purposes. Also, the yields are only moderate.

Likewise, processes involving the electrolytic oxidation of methyl mercaptan can be carried out with difficulty, see Johnson U.S. Pat. No. 2,727,920. There is also described in that patent the reaction of mercaptans with nitric acid, which, however, cannot be employed for large scale processes because of the, in a given case, explosive-like acceleration of the reaction velocity.

It is additionally known to use hydrogen peroxide as the oxidizing agent. This reaction only runs with difficulty unless carboxylic acids are present. Consequently it was thought that the percarboxylic acid formed from the carboxylic acid and the hydrogen peroxide was the true active agent (Showell, J. Org. Chem. Vol. 27 (1962), pages 2853 to 2858). It is particularly disadvantageous in this process that there results a mixture of alkylsulfonic acids with carboxylic acids and in a given case percarboxylic acids from which the alkylsulfonic acids in many cases can be recovered in pure form only with difficulty.

It is also known to carry out the oxidation of alkyl mercaptans or, in a given case, dialkyl disulfides with hydrogen peroxide in a medium which results when carboxylic acids are converted to percarboxylic acids using excess hydrogen peroxide in an alkylsulfonic acid as solvent and the percarboxylic acids formed separated off (Nielsen, German Offenlegungsschrift No. 1,668,585). A disadvantage of carrying out the oxidation in this reaction medium is that this contains considerable amounts of percarboxylic acids so that in this case also, there results alkylsulfonic acids contaminated with carboxylic acids, and in a given case percarboxylic acids.

There has now been found a process for the production of alkylsulfonic acids by the oxidation of alkyl mercaptans or dialkyl disulfides by means of hydrogen peroxide which is characterized by the reaction medium being free of percarboxylic acids (and also free of carboxylic acids). The alkylsulfonic acid resulting from the process of the invention contains water and, in a given case unreacted starting materials but no foreign materials, i.e., no other impurities. They can therefore, be added directly for most purposes. If necessary the pure water free alkylsulfonic acid can be recovered by a simple distillation.

According to the invention, the oxidation by means of hydrogen peroxide is carried out in a reaction medium which is free of percarboxylic acids and which also does not contain carboxylic acids. Such inert reaction media includes the alkylsulfonic acids, which in a given case are diluted with a suitable inert solvent, preferably water. As alkylsulfonic acids there can be used, for example, methanesulfonic acid, ethanesulfonic acid, propanesulfonic acid, butanesulfonic acid, hexanesulfonic acid, octanesulfonic acid or decanesulfonic acid.

It is suitable to always have present that alkylsulfonic acid whose production is planned. It is advantageous to first add to the reaction medium the alkyl mercaptan or dialkyl disulfide and then, to add the hydrogen peroxide, if necessary in small portions. The reaction occurs immediately even at room temperature. It proceeds rapidly and with outstanding yields. This is surprising, since according to previous experience in the absence of carboxylic acids or percarboxylic acids the oxidation with hydrogen peroxide is retarded and is only carried out with difficulty.

As alkyl mercaptans, there can be employed, for example, those having 1 to 18, preferably 1 to 6 carbon atoms. Thus, there can be used methyl mercaptan, ethyl mercaptan, propyl mercaptan, isopropyl mercaptan, butyl mercaptan, amyl mercaptan, sec. butyl mercaptan, hexyl mercaptan, hexadecyl mercaptan, octadecyl mercaptan, octyl mercaptan or decyl mercaptan. As dialkyl disulfides there are used, for example, compounds having 2–20, preferably 2–12 carbon atoms. Thus, there can be used dimethyl disulfide, diethyl disulfide, dipropyl disulfide, diisopropyl disulfide, dibutyl disulfide, diamyl disulfide, dihexyl disulfide, dioctyl disulfide or didecyl disulfide.

The concentration of the aqueous hydrogen peroxide solutions are not critical. Thus, there are suitable the commercial solutions with a concentration of hydrogen peroxide of 25–70 weight %, but there are also suitable hydrogen peroxide concentrations up to 90 weight %. Lower concentrations of hydrogen peroxide can also be used, down to 3 weight %. Preferably there are used solutions with a concentration of 10 to 50 weight % of hydrogen peroxide.

The amount of diluent is not critical but, in carrying out the reaction of the invention, it is advantageous to employ an at least 5 fold molar amount of water based on the amount of alkyl mercaptan or dialkyl disulfide used. The water can be used, for example, in a molar amount of 5 to 20 moles per mole of alkyl mercaptan or dialkyl disulfide.

This ratio of water to starting compound should suitably be present at the beginning of the reaction whereupon in a given case portionwise, addition to the aqueous hydrogen peroxide solution depending on the concentration of the added solution there is more or less of a shifting to a larger amount of water.

Preferably, the reaction of the invention can be carried out in the presence of 1 to 35 mole % of alkylsulfonic acid based on the alkyl mercaptan or dialkyl disulfide employed.

The material to be oxidized, i.e., the alkyl mercaptan or dialkyl disulfide, and the hydrogen peroxide can be employed in equivalent amounts, although a excess of either reactant can be employed, first of all, the hydrogen peroxide.

The temperatures at which the process of the invention is carried out depends on the manner of carrying out the process. If a mixture of sulfur compound (alkyl mercaptan or disulfide) and alkylsulfonic acid cooled below its boiling point, in a given case dissolved in water or another solvent, is employed and then hydrogen peroxide added, attention must be paid that there is excluded a temperature increase above the boiling point of the reaction mixture during the addition of the first-third of the equivalent amount of hydrogen peroxide. With too quick an increase in temperature, the heat of reaction can no longer be drawn off and the reaction held under control.

During the addition of the last two-thirds of the equivalent amount of hydrogen peroxide, the temperature of the mixture can increase to the boiling point, i.e., the speed of inflow of hydrogen peroxide is increased in comparison to the first phase of the reaction.

According to another variant of the process, the hydrogen peroxide solution and the alkylsulfonic acid is present as a mixture and then the sulfur-containing compound (mercaptan or disulfide) is fed in.

By heating the reaction is started and by cooling and corresponding regulation of the speed of dosing the sulfur-containing compound, the reaction is held at the boiling temperature and, thus, carried to completion.

In continuous carrying out the process, it is recommended to carry out the reaction in two steps. Hereby the reaction is started according to one of the variants named above in a main reaction vessel and the reactants added preferably in stoichiometrical amounts. The reaction is carried to completion in a subsequent reactor.

In many cases, the alkylsulfonic acid after removal of the excess hydrogen peroxide, can be added and used directly in the concentration produced. If this is not the case, the greatest part of the water is first distilled off under reduced pressure, then the pure distillation of the alkylsulfonic acid can then take place under reduced pressure. Hereby there is readily produced a nearly 100% product.

Unless otherwise indicated all parts and percentages are by weight.

The process of the invention is explained further by the following examples.

EXAMPLE 1

(According to the State of the Art)

There were dropped into 48 grams of methyl mercaptan in 100 grams of water with stirring in the course of 3 hours 287 ml of a 32% aqueous hydrogen peroxide solution. Subsequently, the reaction mixture was held for one hour at the boiling temperature.

No reaction of the methyl mercaptan with the hydrogen peroxide took place.

EXAMPLE 2

(According to the Invention)

There were added to 48 grams of methyl mercaptan and 5 grams of methanesulfonic acids in 100 grams of water with stirring in the course of 2.5 hours 287 ml of a 32% aqueous hydrogen peroxide solution in such manner that the temperature of the preliminary mixture increased from 6° C. to 90° C. The reaction mixture was held for one-half hour at 100° to 110° C. At this point the hydrogen peroxide added was reacted to the extent that only 0.1% was left unreacted.

The distillation of the reaction product gave an 88% yield of pure (100%) methanesulfonic acid.

EXAMPLE 3

(According to the Invention)

There were dropped into 48 grams of methyl mercaptan and 20 grams of methanesulfonic acid in 100 grams of water with stirring in the course of 2.5 hours 287 ml of a 32% aqueous solution of hydrogen peroxide in such manner that the temperature of the preliminary mixture increased from 6° C. to 90° C.

The reaction mixture was heated for one-half hour at 100° to 110° C. At this point only 0.5% of the hydrogen peroxide added was unreacted.

The distillation of the reaction product resulted in a yield of 95% of pure (100%) methanesulfonic acid.

EXAMPLE 4

(According to the Invention)

There were dropped into 189 grams of dimethyl disulfide and 30 grams of methanesulfonic acid in 200 grams of water with stirring in the course of 2.5 hours 974 ml of a 32% aqueous solution of hydrogen peroxide in such manner that the temperature of the preliminary mixture increased from 6° C. to 90° C.

The reaction mixture was heated for one-half hour at a temperature of 100° to 110° C. At this point only 0.5% of the hydrogen peroxide added was unreacted.

The distillation of the reaction product resulted in a yield of 89% of 100% pure methanesulfonic acid.

EXAMPLE 5

(According to the Invention)

There were dropped into 118 grams of hexyl mercaptan and 30 grams of hexanesulfonic in 100 grams of water with stirring in the course of 2.5 hours 287 ml of a 32% aqueous solution of hydrogen peroxide in such manner that the temperature of the preliminary mixture increased from 6° C. to 96° C.

The reaction mixture was heated for one-half hour at a temperature of 100° to 110° C. At this point only 0.1% of the hydrogen peroxide added was unreacted.

The distillation of the reaction product resulted in a yield of 85% of 100% pure hexanesulfonic acid.

The process can comprise, consist essentially of, or consist of the steps set forth using the stated materials.

What is claimed is:

1. A process for the production of an alkylsulfonic acid comprising oxidizing an alkyl mercaptan or a dialkyl disulfide with hydrogen peroxide in a liquid alkylsulfonic acid reaction medium free of percarboxylic acids and carboxylic acids, there being employed 1 to 35% of alkylsulfonic acid based on the amount of alkyl mercaptan or dialkyl disulfide.

2. The process of claim 1 wherein the alkyl mercaptan has 1 to 18 carbon atoms and the dialkyl disulfide has 2 to 20 carbon atoms.

3. The process of claim 2 wherein the alkyl mercaptan has 1 to 6 carbon atoms and the dialkyl disulfide has 2 to 12 carbon atoms.

4. The process of claim 3 wherein there is employed methyl mercaptan.

5. The process of claim 1 wherein the reaction is carried out employing water as a diluent.

6. The process of claim 5 wherein there is employed an at least 5-fold molar amount of water based on the amount of alkyl mercaptan or dialkyl disulfide employed.

7. The process of claim 1 wherein the materials employed consist of (1) the alkyl mercaptan or dialkyl disulfide (2) the alkylsulfonic acid, (3) hydrogen peroxide and (4) water.

8. The process of claim 2 wherein the reaction is carried out in water.

9. The process of claim 8 wherein there is employed an at least 5-fold molar amount of water based on the amount of alkyl mercaptan or dialkyl disulfide employed.

10. The process of claim 9 wherein there is employed an alkyl mercaptan having 1 to 6 carbon atoms in the alkyl group.

11. The process of claim 9 wherein there is employed a dialkyl disulfide having 2 to 12 carbon atoms.

12. The process of claim 9 wherein the temperature is between 60° C. and the boiling point of the mixture and the hydrogen peroxide is employed in an amount at least equivalent to the alkyl mercaptan or dialkyl disulfide.

13. The process of claim 1 wherein the alkyl mercaptan has 1 to 18 carbon atoms and the dialkyl disulfide has 2 to 20 carbon atoms.

* * * * *